US00PP14309P29

(12) United States Plant Patent
Olesen et al.

(10) Patent No.: US PP14,309 P2
(45) Date of Patent: Nov. 18, 2003

(54) MINIATURE ROSE PLANT NAMED 'POULRA015'

(50) Latin Name: *Rosa hybrida*
Varietal Denomination: POULra015

(75) Inventors: L. Pernille Olesen, Fredensborg (DK); Mogens N. Olesen, Fredensborg (DK)

(73) Assignee: Poulsen Roser APS, Fredensborg (DK)

( * ) Notice: Subject to any disclaimer, the term of this patent is extended or adjusted under 35 U.S.C. 154(b) by 0 days.

(21) Appl. No.: 10/245,931

(22) Filed: Sep. 17, 2002

(51) Int. Cl.[7] ..... A01H 5/00
(52) U.S. Cl. ..... Plt./117
(58) Field of Search ..... Plt./117, 116, 124, Plt./111, 125

*Primary Examiner*—Bruce R. Campell
*Assistant Examiner*—June Hwu

(57) ABSTRACT

A new miniature rose which has abundant, white flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

Classification: Botanical: *Rosa hybrida* POULra015. Commercial: Miniature.

The present invention constitutes a new and distinct variety of miniature rose plant which originated from a controlled crossing between 'Patricia Kordana', described and illustrated in U.S. Plant Pat. No. 11,242, issued on Feb. 22, 2000 and an unnamed, non-patented seedling. The two parents were crossed and the resulting seeds were planted in a controlled environment. The new variety is named 'POULra015'.

The new rose may be distinguished from its seed parent, 'Patricia Kordana', by the following combination of characteristics:

1. The bloom color of 'Patricia Kordana' is pink, while that of 'POULra015' is white.
2. 'Patricia Kordana' has a petal count of 25 to 30, while that of 'POULra015' is 13 to 15.

The new variety may be distinguished from its pollen parent, an unnamed seedling, created by the same inventors, by the following combination of characteristics:

1. The unnamed seedling has a stronger fragrance than does 'POULra015'.
2. The unnamed seedling has more greenish-white blooms, while those of 'POULra015' are a more ivory white.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULra015' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULra015' was selected by the inventors as a single plant from the progeny of the hybridization in June of 1998.

Asexual reproduction of 'POULra015' by cuttings and traditional budding was first done by L. Pernille and Mogens N. Olesen in their nursery in Fredensborg, Denmark in April of 1999. This initial and other subsequent propagations conducted in controlled environments have demonstrated that the characteristics of 'POULra015' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULra015'. Specifically illustrated in SHEET 1:

1. Stem showing branching and the attachment of leaves, buds, and peduncles;
2. Flower bud, partially opened bud, and open bloom;
3. Flower petals, detached;
4. Sepals, receptacle, and pedicel;
5. Stem as well as a bare stem exhibiting thorns;
6. Leaves.

DETAILED DESCRIPTION OF THE VARIETY

The following is a description of 'POULra015', as observed in its growth in a field nursery in Jackson County, Oreg. Color references are made using The Royal Horticultural Society (London, England) Colour Chart, 1995, except where common terms of color are used.

For a comparison, several physical characteristics of the rose variety 'POULezy', a rose variety from the same inventors described and illustrated in U.S. Plant Pat. No. 10,737 and issued on Dec. 29, 1998 are compared to 'POULra015' in Chart 1.

CHART 1

| | 'POULra015' | 'POULezy' |
|---|---|---|
| Petal count | 13 to 15 petals. | 30 to 40 petals. |
| Fragrance: | Faint. | Moderate. |
| Thorn incidence: | None. | Few. |

Parents: 'Patricia Kordana'×Unnamed seedling.

FLOWER AND FLOWER BUD

Blooming habit: Recurrent.

Flower bud:

*Size.*—Upon opening, 21 mm in length from base of receptacle to end of bud.

*Bud form.*—Pointed ovoid.

*Bud color.*—As sepals unfold, upper surface of petals is Yellow-White Group 158C; lower surface is Yellow-White Group 158D. At ¼ opening, upper surface of petals is Yellow-White Group 158D; lower surface is Yellow-White Group 158D. Guard petals exhibit occasional red intonation.

*Sepals.*—Yellow-Green Group 144A. Medium foliaceous appendages on three of the five sepals. Surfaces of sepals are slightly pubescent. Stipitate glands are present in very limited quantities. Shape: Sepal apex is cirrose. Base is flat at union with receptacle. Size: 20 mm long and 10 mm wide.

*Receptacle.*—Surface: Smooth. Shape: Funnel-shaped. Size: 5 mm (h)×5 mm (w). Color: Yellow-Green Group 144A and B.

*Peduncle.*—Surface: Scant stipitate glands present. Length: 40 to 45 mm average length. Color: Yellow-Green Group 144 A and B. Strength: Strong.

*Borne.*—Singly.

*Anthocyanin.*—Present on peduncle when grown under high light conditions. Greyed-Purple Group 185D.

Flower bloom:

*Fragrance.*—Very light.

*Duration.*—As a pot plant, flowers last from 6 to 8 days. Petals fall cleanly away from plant.

*Size.*—Medium for a 10 to 12 cm pot rose. Average flower diameter is 55 mm when open.

*Form.*—Shape of flower when viewed from the side: Upon opening, upper part: Flattened convex. Upon opening, lower part: Flat. Open flower, upper part: Convex. Open flower, lower part: Flat.

*Petalage.*—13 to 15 petals under normal conditions with 0 to 3 petaloids.

Color:

*Upon opening, petals.*—Outermost petals: Outer Side: Yellow Group 11D. Inner Side: Yellow Group 11D. Innermost petals: Outer Side: Yellow Group 11D. Inner Side: Yellow Group 11D.

*Upon opening, basal petal spots.*—Outermost petals: Outer Side: Yellow Group 1D. Inner Side: Yellow Group 1D. Innermost petals: Outer Side: Yellow Group 1D. Inner Side: Yellow Group 1D.

*After opening, petals.*—Outermost petals: Outer Side: Yellow Group 11D. Inner Side: Yellow Group 11D. Innermost petals: Outer Side: Yellow Group 11D. Inner Side: Yellow Group 11D.

*After opening, basal petal spots.*—Outermost petals: Outer Side: Yellow Group 1D. Inner Side: Yellow Group 1D. Innermost petals: Outer Side: Yellow Group 1D. Inner Side: Yellow Group 1D.

General tonality: On open flower Yellow Group 11D. No change in the general tonality at the end of the $7^{th}$ day. Afterwards, general tonality is White Group 155B.

Petals:

*Petal reflex.*—Slight.

*Petal edge.*—Ruffled.

*Shape.*—Apex: Rounded. Base: Rounded.

*Petaloids.*—Quantity: 0 to 3. Size: 18 mm long; 15 to 20 mm wide. Color: Yellow Group 11D.

*Thickness.*—Average.

*Arrangement.*—Informal.

Reproductive organs:

*Pistils.*—Length: 5 to 6 mm long. Quantity: 30 to 35.

*Pollen.*—Color: Yellow Group 13A. Quantity: Scant.

*Anthers.*—Size: 1–2 mm long. Color: Yellow Group 13A. Quantity: 32.

*Filaments.*—Color: Yellow-Green Group 154D. Length: 5 to 8 mm.

*Stigmas.*—Slightly superior in location to anthers. Color: Greyed-Purple Group 186B.

*Styles.*—Color: Yellow-Green Group 154D.

*Seed formation.*—Hips: None observed.

PLANT

Plant growth: Moderate, compact, upright to bushy. When grown as a 10 cm pot plant, the average height of the plant is 25 cm and the average width is 20 to 25 cm.

Stems:

*Color.*—Young wood: Yellow-Green Group 144A. Older wood: Yellow-Green Group 144A.

*Prickles.*—Incidence: 0 per 10 cm of stem.

*Surface.*—Young wood: Smooth. Older wood: Smooth.

Plant foliage: Typical number of leaflets on leaves in middle of the stem: 5 leaflets.

*Leaf size.*—85 mm (l)×45 mm (w).

*Quantity.*—Average.

*Color.*—Upper Leaf Surface: Yellow-Green Group 146A. Lower Leaf Surface: Yellow-Green Group 146B. Juvenile foliage: Upper Leaf Surface: Green Group 137A. Lower Leaf Surface: Green Group 138B.

Plant leaves and leaflets:

*Stipules.*—Size: 10 to 12 mm. Color: Yellow-Green Group 144 B and C. Stipitate glands: Present on edges of stipules.

*Petiole.*—Length: 10–14 mm. Color: Yellow-Green Group 146B. Underneath: Yellow-Green Group 144B. Margins: Yellow-Green Group 146B.

*Rachis.*—Color: Yellow-Green Group 146B. Underneath: Yellow-Green Group 144B. Margins: Yellow-Green Group 146B.

*Leaflet.*—Edge: Serrated. Shape: Apex: Acute. Base: Acute. Texture: Matte finish. Thickness: Thin. Arrangement: Odd pinnate. Venation: Reticulate.

Disease resistance: Average resistance to mildew, black spot, and Botrytis under normal growing conditions in Jackson County, Oreg.

We claim:

1. A new and distinct variety of rose plant of the miniature class, substantially as herein illustrated and described as a distinct and novel rose variety due to its abundant, white flowers, vigorous growth, compact habit, suitability for production from softwood cuttings in pots, and durable flowers and foliage which make the variety suitable for distribution in the floral industry.

* * * * *

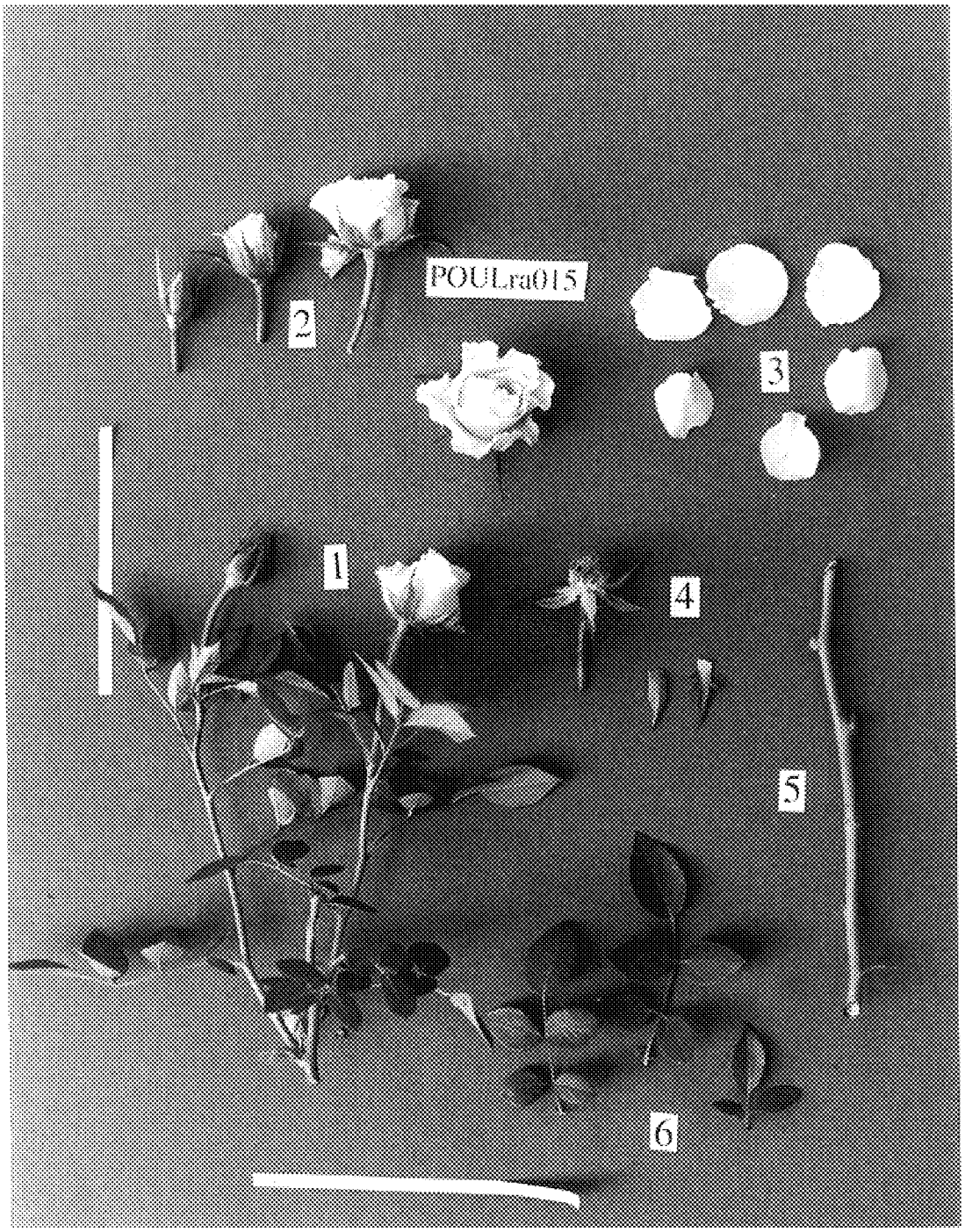
POULra015
1
2
3
4
5
6